(12) United States Patent  (10) Patent No.: US 6,432,092 B2
Miller  (45) Date of Patent: *Aug. 13, 2002

(54) TISSUE MAPPING INJECTION DEVICE

(75) Inventor: Eric C. Miller, Los Gatos, CA (US)

(73) Assignee: Tyco Healthcare Group LP, Norwalk, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 12 days.

(21) Appl. No.: 09/478,552

(22) Filed: Jan. 6, 2000

Related U.S. Application Data

(60) Provisional application No. 60/114,824, filed on Jan. 6, 1999.

(51) Int. Cl.[7] ............................................... A61M 5/00
(52) U.S. Cl. ....................... 604/272; 604/264; 604/515; 604/164.12
(58) Field of Search ................................ 604/272, 264, 604/515, 158, 164.12, 163

(56) References Cited

U.S. PATENT DOCUMENTS

| | | | |
|---|---|---|---|
| 4,416,660 A | * 11/1983 | Dafoe | ........................ 604/515 |
| 5,026,350 A | 6/1991 | Tanaka et al. | |
| 5,152,749 A | * 10/1992 | Giesy et al. | ................. 604/164 |
| 5,354,279 A | * 10/1994 | Hofling | ........................ 604/164 |
| 5,419,777 A | * 5/1995 | Hofling | ........................ 604/264 |
| 5,464,395 A | * 11/1995 | Faxon et al. | ................... 604/96 |
| 5,910,133 A | * 6/1999 | Gould | ..................... 604/272 X |

FOREIGN PATENT DOCUMENTS

| | | |
|---|---|---|
| EP | 834288 A | 4/1998 |
| GB | 2269538 A | 2/1994 |
| GB | 2327614 A | 2/1999 |
| WO | WO 96/29946 A | 10/1996 |

* cited by examiner

Primary Examiner—John D. Yasko

(57) ABSTRACT

A tissue mapping injection device suitable for use during a lymphatic breast mapping procedure is provided. The device includes a housing having an elongated body portion extending distally therefrom. A plunger is slidably positioned within the housing. A connector rod is secured to the forward end of the plunger and extends distally through the elongated body portion. The plunger and the connector rod define a fluid delivery channel. A plurality of needles are secured to the distal end of the connector rod. Each of the needles is constructed from a shape memory material and defines a fluid injection channel which communicates with the fluid delivery channel. The plunger is movable from a retracted position wherein the needles are positioned within the elongated body portion to an advanced position wherein the needles extend outwardly from the distal end of the elongated body portion.

20 Claims, 7 Drawing Sheets

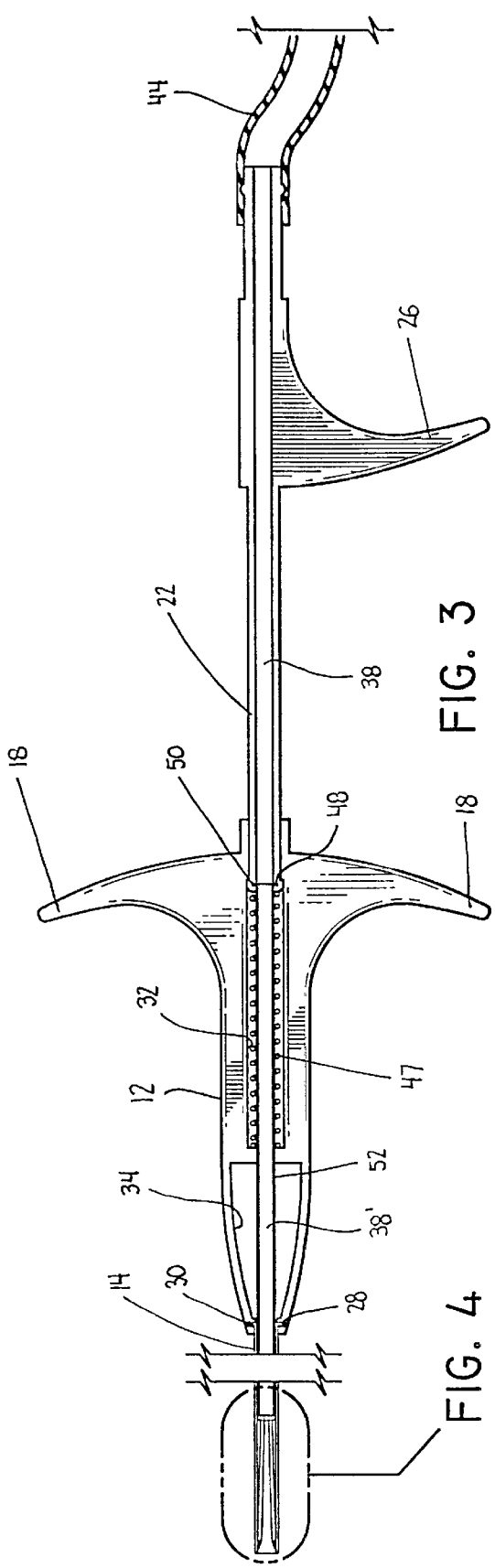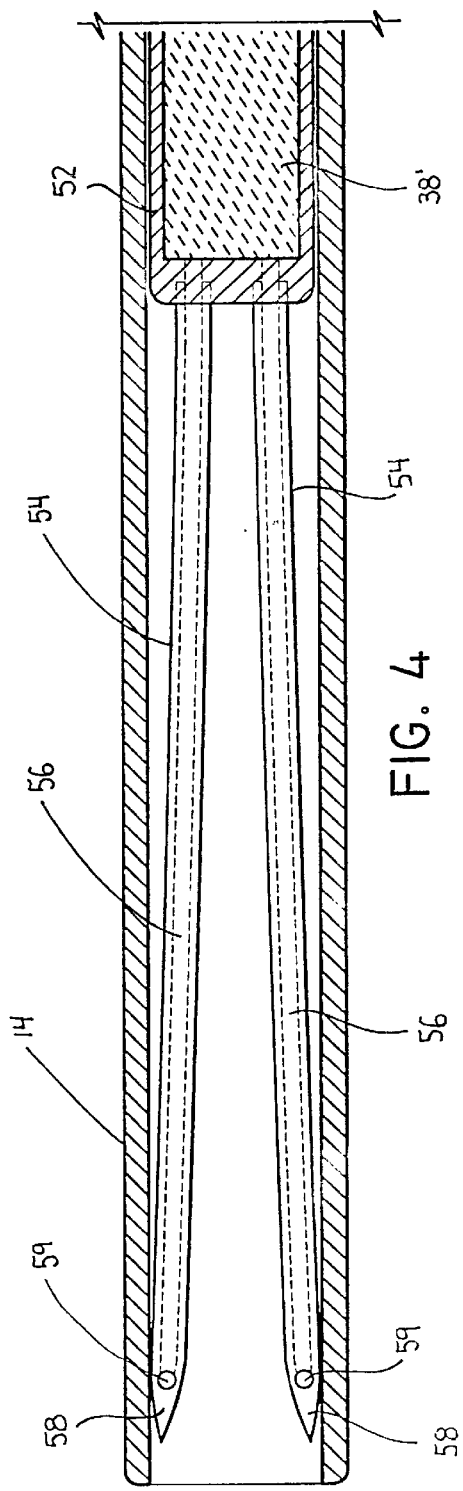

TISSUE MAPPING INJECTION DEVICE

CROSS REFERENCE TO RELATED APPLICATION

This application claims priority from U.S. provisional application Ser. No. 60/114,824, filed Jan. 6, 1999, which is hereby incorporated by reference.

BACKGROUND

1. Technical Field

The present disclosure relates generally to a surgical instrument for injecting a fluid into tissue and, more particularly to a surgical instrument for injecting an imaging radio label material into breast tissue for the detection of breast carcinoma.

2. Background of Related Art

Breast carcinoma is the most common cancer and the second leading cause of cancer-related death in women living in the United States. The incidence of breast cancer is increasing by about three percent per year. Recent studies show that one in eight women in the United States will develop breast cancer. Early detection lowers mortality and prolongs life expectancy of those having breast cancer.

Presently, standard screening tests for early detection of breast cancer include breast self-examination, breast examination by a physician, and mammography. In general, physical examination alone will detect, at best, only sixty to eighty percent of breast masses, whereas mammography will detect eighty to ninety percent of breast masses in women not having dense breasts. In women having dense breasts, mammography has a false-negative rate of twenty-five to forty-five percent, and has a positive predictive value of only thirty percent. Only one in every four to six biopsies performed to confirm or rule out malignancy of suspicious lesions detected during mammograms will be malignant. Thus, the majority of biopsies prove to be unnecessary, i.e., the lesion is benign. Considering that the economic cost as well as the physical and psychological stress of undergoing a biopsy is high, the need for a noninvasive and accurate technique to better discriminate between benign and malignant mammographic abnormalities which require biopsy is clearly present.

One such technique being developed for noninvasively and accurately discriminating between malignant and benign mammographic abnormalities is Lymphatic Breast Mapping ("LBM"). During an LBM procedure, a quantity of radioactive tracer or dye is injected into and around a tumor. Because of the tracer's biochemistry, the tumor will collect more of the tracer than does normal healthy tissue. Thus, when the radioactive tracer decays and emits gamma rays, a higher number of these gamma rays will originate from tumor sites than from equal volumes of healthy tissue. The tracer distribution and gamma ray emission can be identified using a scintillation camera to enable doctors to identify the presence or absence of cancer.

Accordingly, a need exists for a surgical instrument for injecting a radioactive tracer into body tissue at precise locations adjacent a tumor.

SUMMARY

In accordance with the present disclosure, a tissue mapping injection device is disclosed that is capable of injecting an imaging radio label material or dye into the body at a location encompassing target tissue. The injection device includes a housing, an elongated body portion coupled to and extending distally from the housing, an actuator assembly slidably supported within the housing from a retracted to an advanced position, and at least one needle coupled to the distal end of the actuator assembly. The actuator assembly includes a plunger which is slidably positioned along a cylindrical bore formed within the housing. An engagement member is coupled to or monolithically formed with the plunger and is positioned to be engaged by the thumb of a surgeon. The plunger has a first end which extends distally from one end of the housing in a direction opposite to the elongated body portion. The plunger defines a fluid delivery channel and includes a distal end adapted to receive a fluid delivery hose.

A connector rod is coupled to and extends from the plunger through the elongated body portion. The connector rod also defines a fluid delivery channel which communicates with the plunger delivery channel. The needles are connected to the distal end of the connector rod and are formed from a shape memory material. Each of the needles defines an injection delivery channel which communicates with the fluid delivery channel of the connector rod. In a relaxed state, the needles curve outwardly at a predetermined angle relative to the longitudinal axis of the elongated body portion. In one embodiment, four needles are secured to the distal end of the connector rod. Each of the needles is substantially identically shaped in its relaxed state.

In use, when the plunger is in the retracted position, the needles are positioned within elongated body portion and are deformed by the body portion to a substantially straight configuration. When the plunger is moved to the advanced position, the needles are moved distally out of the distal end of the elongated body portion. The needles are no longer deformed by the elongated body portion and thus, return to the relaxed state curving outwardly from the longitudinal axis of the body portion. Since each of the needles is similarly shaped, the tips of the needles lie in a common plane and extend into four quadrants surrounding a target tissue. Each of the needles is spaced approximately 90° from adjacent needles. Fluid can be injected into the tissue surrounding the target tissue via the delivery channels in the plunger and the injection channel formed in the needles.

In an alternate embodiment, eight needles are secured to the distal end of the connector rod. The eight needles form two sets of four needles, wherein each needle has a substantially identical configuration in the relaxed state as the other needles in that set of needles. When the needles are advanced out of the distal end of the elongated body portion, the tips of the first set of needles lie in a first plane and the tips of the second set of needles lie in a second plane spaced from the first plane. Each of the needles of each set of needles extends into one of the four quadrants surrounding a target tissue and is spaced approximately ninety degrees from adjacent needles.

BRIEF DESCRIPTION OF THE DRAWINGS

Various preferred embodiments of the injection device for Lymphatic Breast Mapping are described herein with reference to the drawings, wherein:

FIG. 3 is a side view of the injection device shown in FIG. 1 with parts removed in a non-deployed condition;

FIG. 4 is an enlarged view of the indicated area of detail shown in FIG. 4;

DETAILED DESCRIPTION OF PREFERRED EMBODIMENTS

Figure 1:
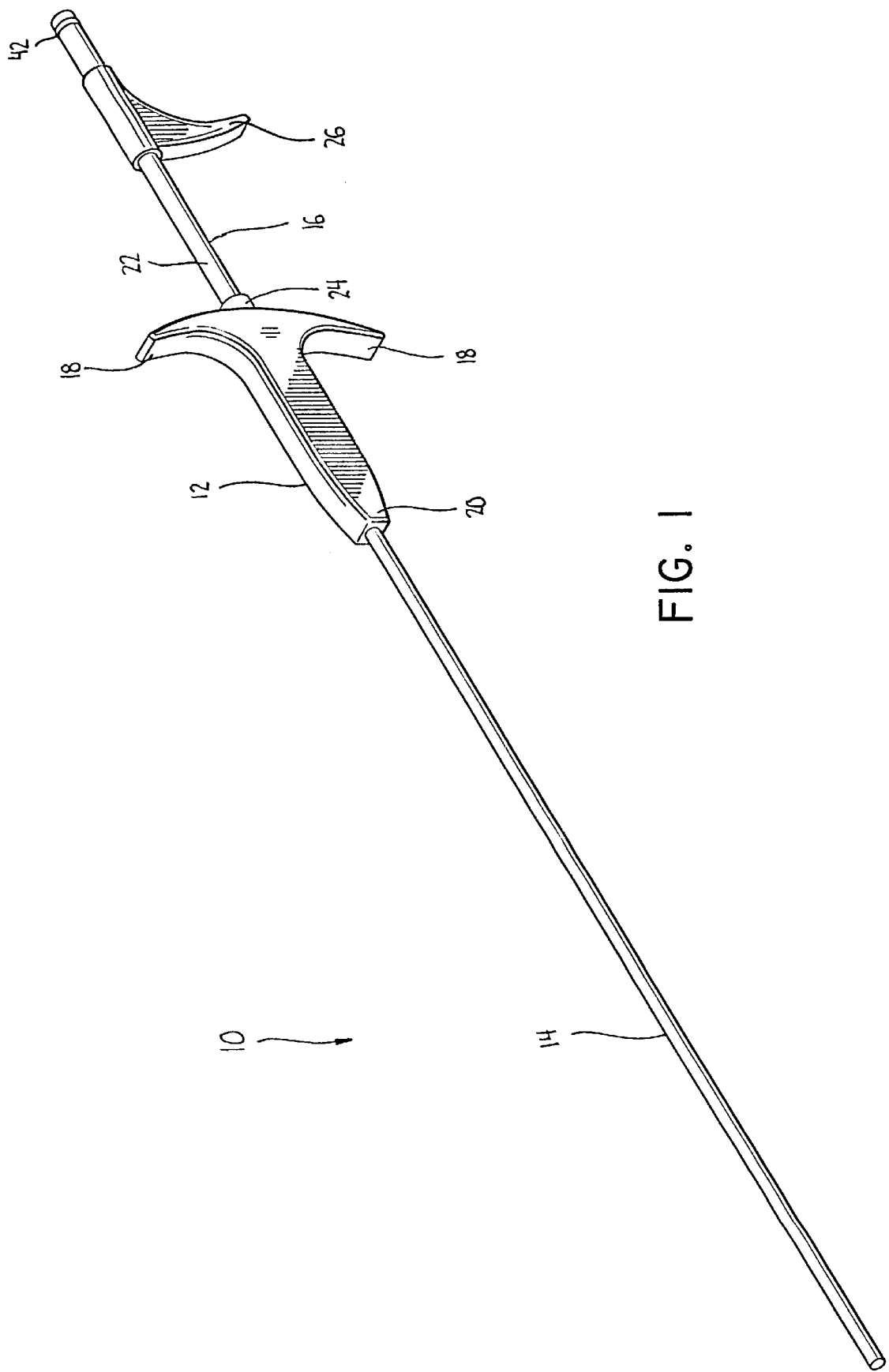
FIG. 1 is a perspective view of one embodiment of the injection device in a non-deployed condition.

Preferred embodiments of the presently disclosed injection device will now be described in detail with reference to the drawings, in which like reference numerals designate identical or corresponding elements in each of the several views.

FIGS. 1–4 illustrate the injection device shown generally as 10. Briefly, injection device 10 includes a housing 12, an elongated body portion 14, and an actuator assembly 16. Housing 12 has a pair of radially extending fingers 18 configured to be engaged by the fingers of a surgeon. Elongated body portion 14 is fixedly secured to one end 20 of housing 12 and extends distally therefrom. Actuator assembly 16 includes a plunger 22 which is slidably positioned within housing 12 and extends distally from the other end 24 of housing 12 in a direction opposite to body portion 14. An engagement member 26 is secured to plunger 22 at a location to be grasped by the thumb of a surgeon while the surgeon's fingers grip radially extending fingers 18. Alternately, engagement member 26 can be monolithically formed with plunger 22.

Figure 2:
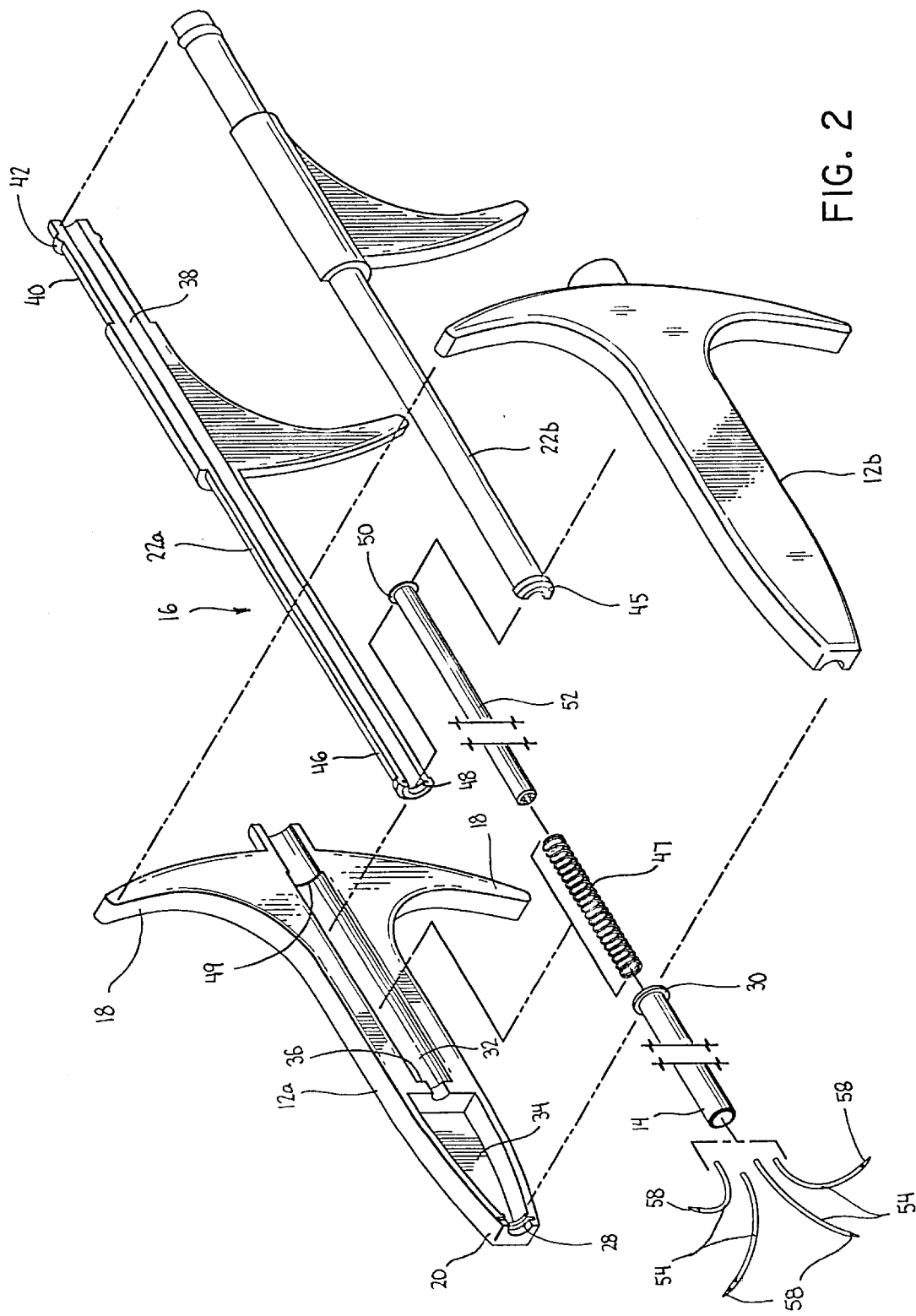
FIG. 2 is a perspective view with parts separated of the injection device shown in FIG. 1.

Referring to FIG. 2, housing 12 includes a pair of molded housing half-sections 12a and 12b which are secured together via known techniques, e.g., adhesives, ultrasonic welding, screws, etc., to form the housing. End 20 of housing 12 includes a slot 28 configured and dimensioned to receive an annular flange 30 formed at the proximal end of body portion 14. Housing 12 also includes a cylindrical bore 32 and a void 34. Cylindrical bore 32 is dimensioned to slidably receive plunger 22 (FIG. 1). A shoulder 36 is formed at one end of cylindrical bore 32 to limit the extent of longitudinal movement of plunger 22 along bore 32 within housing 12. Void 34 reduces the amount of material required to manufacture the housing and, thus reduces the cost of manufacturing the housing.

Plunger 22 of actuator assembly 16 is preferably formed from molded half-sections 22a and 22b which are secured together using known techniques, e.g., adhesives, ultrasonic welding, screws, etc. Plunger 22 defines a fluid delivery channel 38. A first end 40 of plunger 22 includes an annular rib 42 to facilitate attachment of a fluid supply line 44 (FIG. 3) to the plunger. A second end 46 of plunger 22 has a slot 48 formed therein dimensioned to receive a flange 50 formed at a proximal end of connector rod 52 to secure connector rod 52 in a longitudinally fixed position with respect to plunger 22. The second end 46 of plunger 22 also includes an annular flange 45 dimensioned to engage a biasing member 47 positioned in the forward end of cylindrical bore 32. Biasing member 47, which is preferably a coil spring, is positioned between annular flange 45 of plunger 22 and shoulder 36 of housing 12 to urge the plunger to a retracted position. The proximal end of cylindrical bore 32 also includes a shoulder 49 to retain plunger 22 within cylindrical bore 32.

Referring also to FIGS. 3 and 4, connector rod 52 has a longitudinal axis which is coaxial with the longitudinal axis of plunger 22 and elongated body portion 14. Connector rod 52 extends from end 46 of plunger 22 through elongated body 14 and defines a fluid delivery channel 38' (See FIGS. 3 and 4) which communicates with fluid delivery channel 38. A plurality of hollow needles 54 are secured to the distal end of connector rod 52. Each of the needles defines an injection channel 56 in fluid communication with delivery channel 38'. Each of needles 54 is constructed from a shape memory material and includes a sharpened tip 58 having an outlet orifice 59. Preferably, the shape memory material is Nitinol although other shape memory materials may be used. In the relaxed state, each needle curves outwardly such that a tangent extending from needle tip 58 forms an angle of about ninety (90) degrees with respect to the longitudinal axis of the elongated body 14. Alternately, other needle configurations are envisioned, e.g., needle tip may extend outwardly at an angle of between about 10 degrees to about 150 degrees. The needles 54 are secured to connector rod 52 such that when they are deployed from within elongated body 14, the needles extend away from each other into four planar quadrants surrounding target tissue. Preferably, the needles are positioned at ninety degree intervals about the longitudinal axis of the elongated body portion 14, although different spacings are envisioned.

Referring to FIGS. 3 and 4, when plunger 22 is in its retracted position, connector rod 52 and needles 54 are positioned within elongated body 14. In this position, the inner wall of elongated body 14 urges the needles from a normally curved configuration to a substantially straight configuration.

Figure 5:
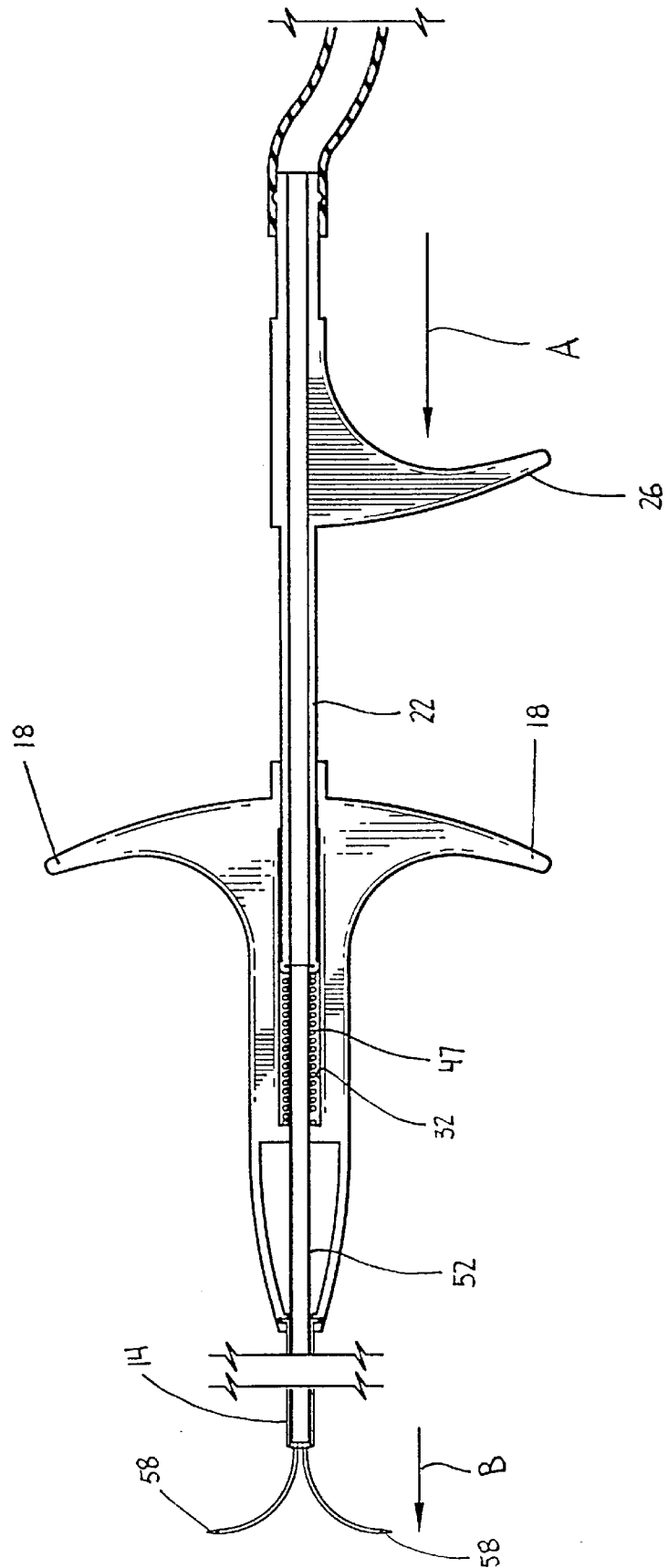
FIG. 5 is a side view of the injection device shown in FIG. 1 with parts removed and in a deployed condition.

Referring to FIG. 5, when engagement member 26 is moved towards housing 12 in the direction indicated by arrow "A", plunger 22 is moved towards the distal end of cylindrical bore 32 against the bias of spring 47. Longitudinal advancement of plunger 22 within cylindrical bore 32 causes corresponding longitudinal advancement of connector rod 52 within elongated body portion 14. As connector rod 52 is advanced, needles 54 are advanced in the direction indicated by arrow "B" in FIG. 5 from a position within elongated body portion 14 to a position extending outwardly from the distal end of elongated body portion 14. As needles 54 exit the distal end of body portion 14, the needles return to a relaxed state wherein the needle tip 58 is pointed in a direction substantially perpendicular to the longitudinal axis of the elongated body portion 14. In the relaxed state, each of needle tips 58 lies in the same vertical plane. See FIG. 6.

Figures 6, 6A:
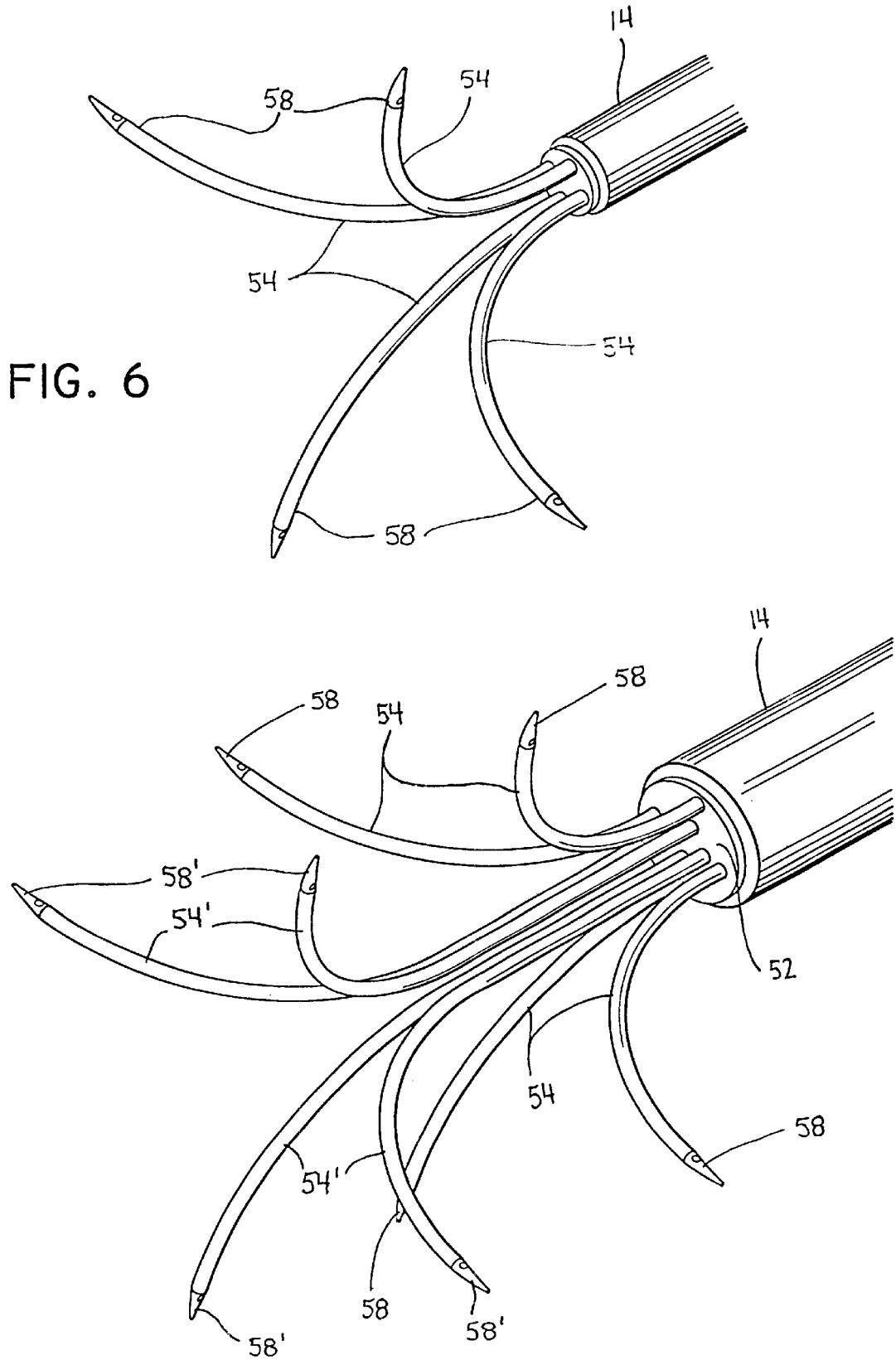
FIG. 6 is a perspective view of the distal end of the injection device shown in FIG. 1 in the deployed condition.
FIG. 6A is an alternate embodiment of the distal end of the injection device shown in FIG. 1 in the deployed condition.

FIG. 6A illustrates an alternate embodiment of the injection device. In the embodiment shown in FIG. 6A, the injection device has eight needles. In the relaxed state, four of the needles 54 extend away from each other into four planar quadrants surrounding target tissue and have tips 58 which lie in a first vertical plane and, four of the needles 54' extend away from each other into four planar quadrants surrounding target tissue and have tips 58' which lie in a second vertical plane spaced from the first vertical plane. By providing additional needles, radioactive tracer or dye can be injected about the entire location of the target tissue.

Figure 7:
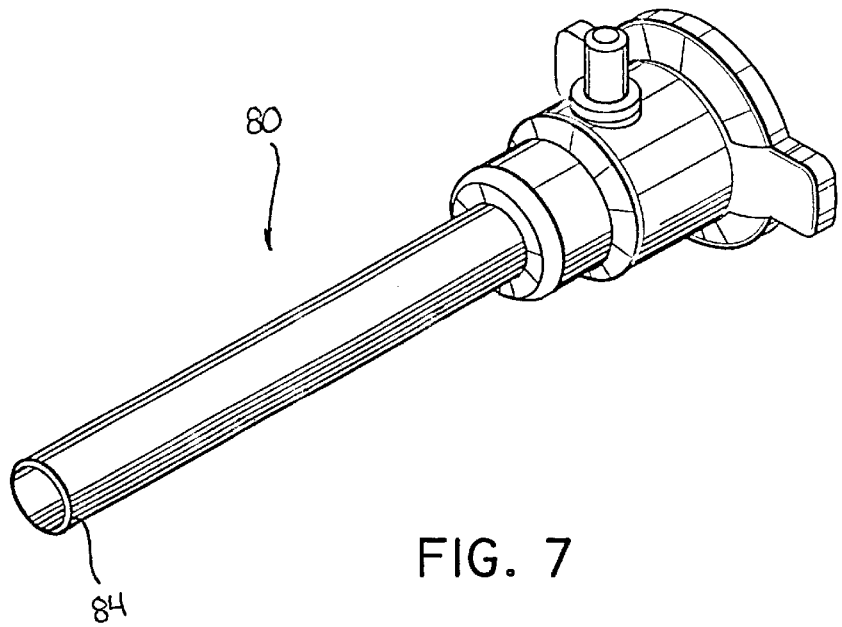
FIG. 7 is a cannula suitable for use with the injections device shown in FIGS. 1 and 6A.
Figure 8:
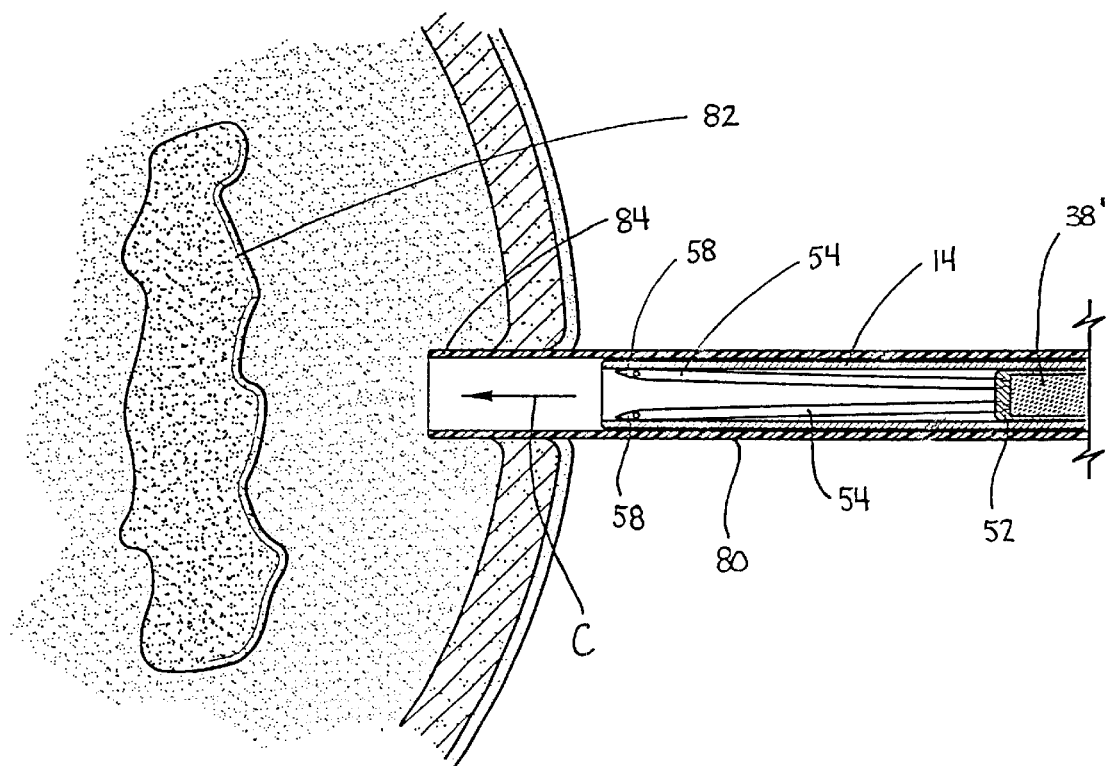
FIG. 8 is a side cross-sectional view of the injection device shown in FIG. 1 in a non-deployed condition passing through the cannula shown in FIG. 7 with the cannula extending partially into body tissue.
Figure 9:
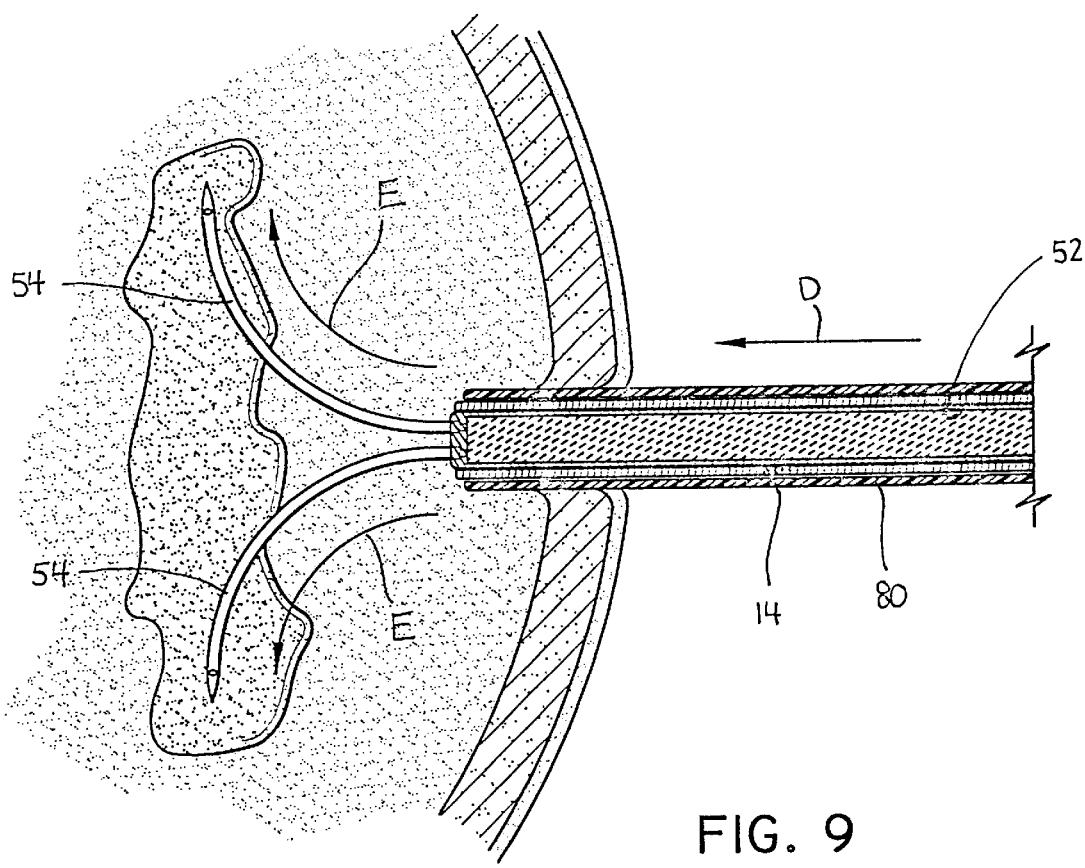
FIG. 9 is a side cross-sectional view of the injection device shown in FIG. 1 in a deployed condition passing through the cannula shown in FIG. 7 with the cannula extending partially into body tissue.

Referring to FIGS. 7–9, during performance of a lymphatic breast mapping procedure, a cannula 80 (FIG. 7) is inserted into tissue via known techniques adjacent the location of the target tissue 82. Next, the elongated body portion 14 of injection device 10 is inserted through cannula 80 in the direction indicated by arrow "C" in FIG. 8 to a position in which the distal end of elongated body portion 14 is located adjacent to the distal end 84 of cannula 80. Finally, actuator assembly 16 is actuated in the manner discussed above to advance connector rod 52 and needles 54 in the direction indicated by arrows "D" and "E", respectively, in FIG. 9, into or adjacent the target tissue. A radioactive tracer or dye 90 can now be injected in and about the location of the target tissue 82 via fluid supply line 44, fluid delivery channels 38 and 38' and injection channels 56.

It will be understood that various modifications may be made to the embodiments disclosed herein. For example, although the injection device has been disclosed as having four needles which extend into four quadrants about the target tissue, a greater or lesser number of needles may be provided. Moreover, the configuration of the needles in the relaxed state may be different than that disclosed. For example, the needle can have a configuration in which the needle tip extends outwardly at an angle of sixty (60) degrees with respect to the base of the needle. Therefore, the above description should not be construed as limiting, but merely as exemplifications of preferred embodiments. Those skilled in the art will envision other modifications within the scope and spirit of the claims appended thereto.

What is claimed is:

1. A surgical instrument for injecting a fluid into tissue comprising:

a housing;

a hollow elongated body portion extending distally from the housing and defining a lumen having a longitudinal axis, the distal end of the body portion defining an unobstructed opening;

an actuator assembly including a plunger slidably positioned within the housing, the plunger defining a fluid delivery channel; and at least one needle having an injection tip, the at least one needle having a proximal end opposite the injection tip which is operatively connected to the plunger, the at least one needle being positioned within the lumen and defining a fluid injection channel which communicates with the fluid delivery channel, the at least one needle being movable, in response to movement of the plunger, from a deformed position located within the lumen of the elongated body portion through the unobstructed opening of the elongated body portion to a relaxed position located externally of the elongated body portion, wherein in the relaxed position, the injection tip extends outwardly from the elongated body portion to define a predetermined angle with respect to the longitudinal axis of the elongated body portion.

2. A surgical instrument according to claim 1, wherein the predetermined angle is about ninety degrees.

3. A surgical instrument according to claim 1, wherein the at least one needle includes four needles, each of the four needles, in the relaxed position, curving outwardly from the longitudinal axis of the elongated body portion into one of four planar quadrants surrounding target tissue.

4. A surgical instrument according to claim 3, wherein the predetermined angle is about ninety degrees.

5. A surgical instrument according to claim 1, wherein the plunger is slidable within the housing between advanced and retracted positions, wherein when the plunger is in the retracted position, the at least one needle is in the deformed position, and when the plunger is in the advanced position, the at least one needle is in the relaxed position.

6. A surgical instrument according to claim 5, wherein the at least one needle includes four needles, each of the needles in the relaxed position, curving outwardly from the longitudinal axis of elongated body portion into one of four planar quadrants surrounding target tissue.

7. A surgical instrument according to claim 6, wherein the predetermined angle is about ninety degrees.

8. A surgical instrument according to claim 1, wherein the at least one needle includes eight needles each of the needles in the relaxed position, curving outwardly from the longitudinal axis of the elongated body portion into one of four planar quadrants surrounding target tissue.

9. A surgical instrument according to claim 8, wherein four of the needles have injection tips positioned in a first vertical plane and the other four needles have injection tips positioned in a second vertical plane which is spaced from the first vertical plane.

10. A surgical instrument according to claim 9, wherein the predetermined angle is about ninety degrees.

11. A surgical instrument according to claim 5, further including a biasing member supported within the housing, the biasing member being positioned to urge the plunger to the retracted position.

12. A surgical instrument according to claim 1, wherein the at least one needle is formed of a shape memory material.

13. A surgical instrument according to claim 1, wherein the at least one needle includes a plurality of needles.

14. A surgical instrument for injecting fluid into tissue comprising:

a housing;

a hollow elongated body fastened to and extending distally from the housing and defining a longitudinal axis, the elongated body defining a lumen having an unobstructed open distal end communicating with the lumen;

an actuator assembly including a plunger slidably positioned within the housing, the plunger defining a fluid delivery channel;

at least one needle having an injection tip operatively connected to the plunger, the at least one needle defining a fluid injection channel which communicates with the fluid delivery channel of the plunger, the at least one needle being movable, in response to movement of the plunger from a retracted position to an advanced position, from a deformed position located within the lumen of the elongated body portion, through the open distal end of the elongated body, to a relaxed position located externally of the elongated body portion, wherein in the relaxed position, the injection tip extends outwardly from the elongated body portion to define a predetermined angle with respect to the longitudinal axis of the elongated body portion; and a biasing member positioned to urge the plunger to the retracted position.

15. A surgical instrument according to claim 14, wherein the at least one needle is formed from a resilient material.

16. A surgical instrument according to claim 14, wherein the at least one needle includes a plurality of needles.

17. A surgical instrument for injecting a fluid into tissue comprising:

a housing;

a hollow elongated body portion secured to and extending distally from the housing, the hollow elongated body portion defining a lumen having a longitudinal axis, the elongated body portion including an unobstructed open distal end;

an actuator slidably positioned within the housing, the actuator defining a fluid delivery channel; and at least one needle having an injection tip operatively connected to the actuator, the at least one needle defining a fluid injection channel which communicates with the fluid delivery channel, the at least one needle being movable, in response to movement of the actuator from a retracted position to an advanced position, from a deformed position located within the lumen of the elongated body portion, through the open distal end of the elongated body portion, to a relaxed position located externally of the elongated body portion, wherein the actuator and the housing each include a finger engagement member to facilitate movement of the actuator between the retracted and advanced positions.

18. A surgical instrument according to claim 17, wherein the at least one needle includes a plurality of needles.

19. A surgical instrument according to claim 17, wherein the at least one needle is formed from a resilient material.

20. A surgical instrument according to claim 17, wherein in the relaxed position, the injection tip extends outwardly of the longitudinal axis of the hollow elongated body portion.

* * * * *